(12) United States Patent
Ko et al.

(10) Patent No.: US 10,406,453 B2
(45) Date of Patent: Sep. 10, 2019

(54) CANNABINOID EXTRACTION PROCESS USING BRINE

(71) Applicant: NextLeaf Solutions Ltd., Coquitlam (CA)

(72) Inventors: Ryan Delmoral Ko, Coquitlam (CA); Brock Hughes, Port Coquitlam (CA); Krupal Pal, Burnaby (CA); Alexzander Samuelsson, Vancouver (CA)

(73) Assignee: Nextleaf Solutions Ltd., Vancouver (CA)

( * ) Notice: Subject to any disclaimer, the term of this patent is extended or adjusted under 35 U.S.C. 154(b) by 0 days.

(21) Appl. No.: 16/112,033

(22) Filed: Aug. 24, 2018

(65) Prior Publication Data

US 2019/0099696 A1 Apr. 4, 2019

Related U.S. Application Data

(63) Continuation-in-part of application No. 15/993,457, filed on May 30, 2018, which is a continuation of application No. 15/721,344, filed on Sep. 29, 2017, now Pat. No. 9,987,567.

(60) Provisional application No. 62/676,261, filed on May 24, 2018, provisional application No. 62/675,620, filed on May 23, 2018.

(51) Int. Cl.
| | | |
|---|---|---|
| *B01D 11/02* | (2006.01) | |
| *B01D 3/08* | (2006.01) | |
| *B01D 3/40* | (2006.01) | |
| *C07C 37/50* | (2006.01) | |
| *C07C 37/74* | (2006.01) | |
| *C07C 37/00* | (2006.01) | |
| *C07C 37/86* | (2006.01) | |
| *C07C 39/19* | (2006.01) | |
| *B01D 15/00* | (2006.01) | |
| *C07D 311/80* | (2006.01) | |

(52) U.S. Cl.
CPC .......... *B01D 11/0288* (2013.01); *B01D 3/085* (2013.01); *B01D 3/40* (2013.01); *B01D 11/0292* (2013.01); *B01D 15/00* (2013.01); *C07C 37/004* (2013.01); *C07C 37/50* (2013.01); *C07C 37/74* (2013.01); *C07C 37/86* (2013.01); *C07C 39/19* (2013.01); *C07D 311/80* (2013.01); *C07C 2601/16* (2017.05)

(58) Field of Classification Search
CPC .... B01D 11/0288; B01D 3/085; B01D 15/00; B01D 3/40; B01D 11/0292; C07C 37/50; C07C 37/74; C07C 37/86; C07C 37/004; C07C 39/19; C07C 2601/16; C07D 311/80

See application file for complete search history.

(56) References Cited

U.S. PATENT DOCUMENTS

2014/0271940 A1* 9/2014 Wurzer ............... A61K 36/185
424/725

FOREIGN PATENT DOCUMENTS

WO 2013165251 11/2013

OTHER PUBLICATIONS

Canadian Intellectual Property Office Examination Report dated Nov. 20, 2018 issued for the co-pending Canadian application assigned Application No. 3,016,078 with an International Filing Date of Aug. 31, 2018.

* cited by examiner

*Primary Examiner* — John M Mauro
(74) *Attorney, Agent, or Firm* — Damien G. Loveland

(57) ABSTRACT

Raw cannabis plant material is mixed with ethanol and spun-dry to extract cannabinoids. The ethanol may be chilled before adding it to the raw cannabis plant material, and a non-polar solvent stage may be used to increase the yield of the extraction. The resulting crude oil and ethanol with the dissolved cannabinoids is separated from the raw cannabis plant material and filtered to remove particulates, waxes, lipids, fats and dissolved impurities. The ethanol is then evaporated from the resulting mixture of oil and ethanol, and the remaining oil then undergoes brine-washing, decarboxylation and distillation to obtain the cannabinoids and other desirable volatile phytochemicals.

28 Claims, 7 Drawing Sheets

CANNABINOID EXTRACTION PROCESS USING BRINE

CROSS-REFERENCE TO RELATED APPLICATIONS

This application is a continuation-in-part of and claims the benefit of U.S. patent application Ser. No. 15/993,457, filed May 30, 2018, which is a continuation of U.S. patent application Ser. No. 15/721,344, filed Sep. 29, 2017, now U.S. Pat. No. 9,987,567, both incorporated herein in their entirety. It also claims benefit of U.S. provisional patent application No. 62/675,620, filed May 23, 2018 and U.S. provisional patent application No. 62/676,261, filed May 24, 2018, both incorporated herein in their entirety.

TECHNICAL FIELD

This application relates to the extraction of cannabinoids from raw cannabis plant material. More specifically, it relates to the extraction of cannabinoids by means of an ethanol-based method that includes washing the extracted oil with brine.

BACKGROUND

In legal, adult-use markets, sales of extracts are growing ten times faster compared to the sales of dried cannabis, and extracts account for over 60% of revenue. With legalization, consumer preferences are shifting from dried cannabis to extracted cannabis products.

However, the scent and flavors of cannabis can be undesirable in many infused products because of excess lipids, plant matter and impurities present in currently available extracts.

U.S. Pat. No. 9,155,767 to Hospodor et al. relates to the extraction of medicinal cannabis compounds into an eluate, by separating a portion of medicinal cannabis compounds contained within a portion of eluate at a first extraction target level, to provide enough clean solvent to continue extraction operations. A high efficiency concentrator processes eluate from one or more tanks, creating clean solvent when extraction targets are met or when clean solvent is exhausted. This manages eluate concentration levels and limits the quantity of concentrated medicinal cannabis compounds on site at any moment in time.

U.S. Pat. No. 7,700,368 to Flockhart et al. relates to the purification of cannabinoid oil from plant material. The high degree of purity for the final cannabinoid oil extract is obtained using a combination of chromatography techniques and different types of solvent for preparing the cannabinoid oil extract and removing any insoluble impurity therefrom.

This background information is provided to reveal information believed by the applicant to be of possible relevance to the present invention. No admission is necessarily intended, nor should be construed, that any of the preceding information constitutes prior art against the present invention.

SUMMARY OF INVENTION

The present invention is directed to the extraction of cannabinoids from plant material. In particular it relates to mixing dried and ground cannabis plants with ethanol in a wash and spin-dry (WSD) apparatus, followed by filtration, evaporation of ethanol, brine-washing, decarboxylation and distillation.

Disclosed herein is a process for extracting cannabinoids from raw cannabis plant material comprising the steps of: adding ethanol to dried and ground cannabis plant material to form an initial mixture; spinning the initial mixture to separate a crude oil and ethanol mixture from the initial mixture; treating the crude oil and ethanol mixture with media to remove unwanted components therefrom; evaporating ethanol from the treated crude oil and ethanol mixture to leave oil; washing the oil with brine; decarboxylating the brine-washed oil to form decarboxylated oil; and distilling the decarboxylated oil to obtain cannabinoids.

BRIEF DESCRIPTION OF DRAWINGS

The following drawings illustrate embodiments of the invention, which should not be construed as restricting the scope of the invention in any way.

DESCRIPTION

A. Glossary

Cannabidiol (CBD) is one of the active cannabinoids found in cannabis and is used for medicinal purposes.

Cannabimemetics are phytochemicals that act on the cannabinoid receptors within the body but are not derived from the cannabis plant nor are they strictly classified as cannabinoids.

Cannabinoids are a group of chemicals that act on cannabinoid receptors in the body, numerous of which are found in the cannabis plant.

Crude oil is a term for the description of condensed, non-filtered oil, i.e. oil that is non-winterized and not treated via charcoal, clay and silica. The crude oil contains the cannabinoids.

Tetrahydrocannabinol (THC) is a psychotropic cannabinoid and is the main psychoactive ingredient of cannabis. THC also has medicinal uses. THCa is the non-psychoactive form of THC.

WSD (wash and spin-dry) separator—a solvent based extraction system/centrifuge drum used to extract botanical compounds from diverse plant species. The device provides a process in which the plant material is first washed or agitated in solvent, and then spun-dry to separate the extract-laden solvent from the waste biomass. Agitation includes rotating the drum back and forth, for example.

Rotovap—a rotary evaporator.

Winterization refers to the cooling of oil to precipitate and remove unwanted plant fats, waxes, and lipids through cooling and filtering.

B. Overview

Figure 1:
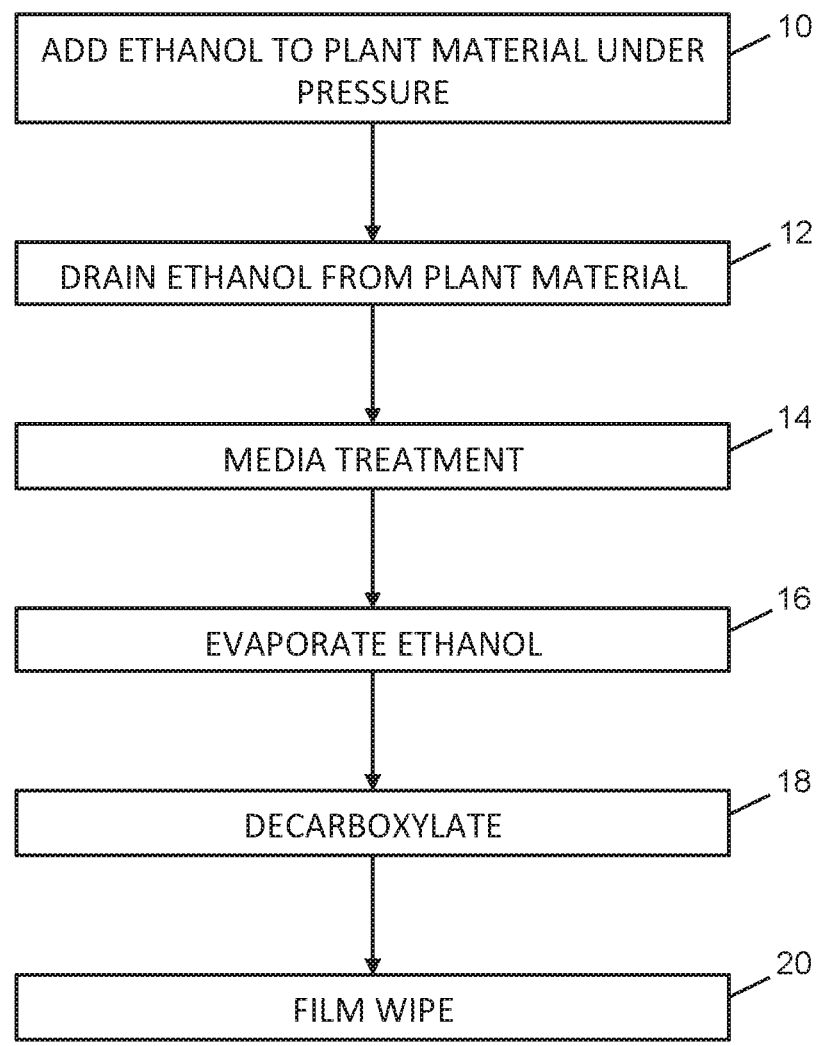
FIG. 1 is a high-level flowchart showing the key steps of a process for extracting cannabinoids according to an embodiment of the present invention.

Referring to FIG. 1, a flowchart of the basic steps of the process is shown. In step 10, a solvent such as ethanol is added to dried and ground cannabis plant material under pressure. The ethanol may be at room temperature or chilled. As a result, the cannabinoids found in the plant material dissolve into the ethanol. In step 12, the ethanol solution is drained from the plant material to form a crude oil and ethanol mixture. The first two steps are considered to be the primary extraction phase.

In step 14, impurities are then removed by media treatment of the crude oil and ethanol mixture, which contains the cannabinoids. In step 16, ethanol is removed or reclaimed from the mixture, by evaporation, for example. Steps 14 and 16 are considered to be the solvent reclamation stage.

In step 18, the oil remaining after the evaporation is decarboxylated to activate the THC. Decarboxylation converts THCa into THC; the process activates the THC by separating the acid component of THCa, the acidic form of the cannabinoid, converting it into THC, the neutral form, by heating to remove the carboxylic acid group and liberate carbon dioxide. The residue after decarboxylation is then, in step 20, distilled using a film wipe apparatus in order to extract the cannabinoids.

C. Exemplary Process

Figure 2:
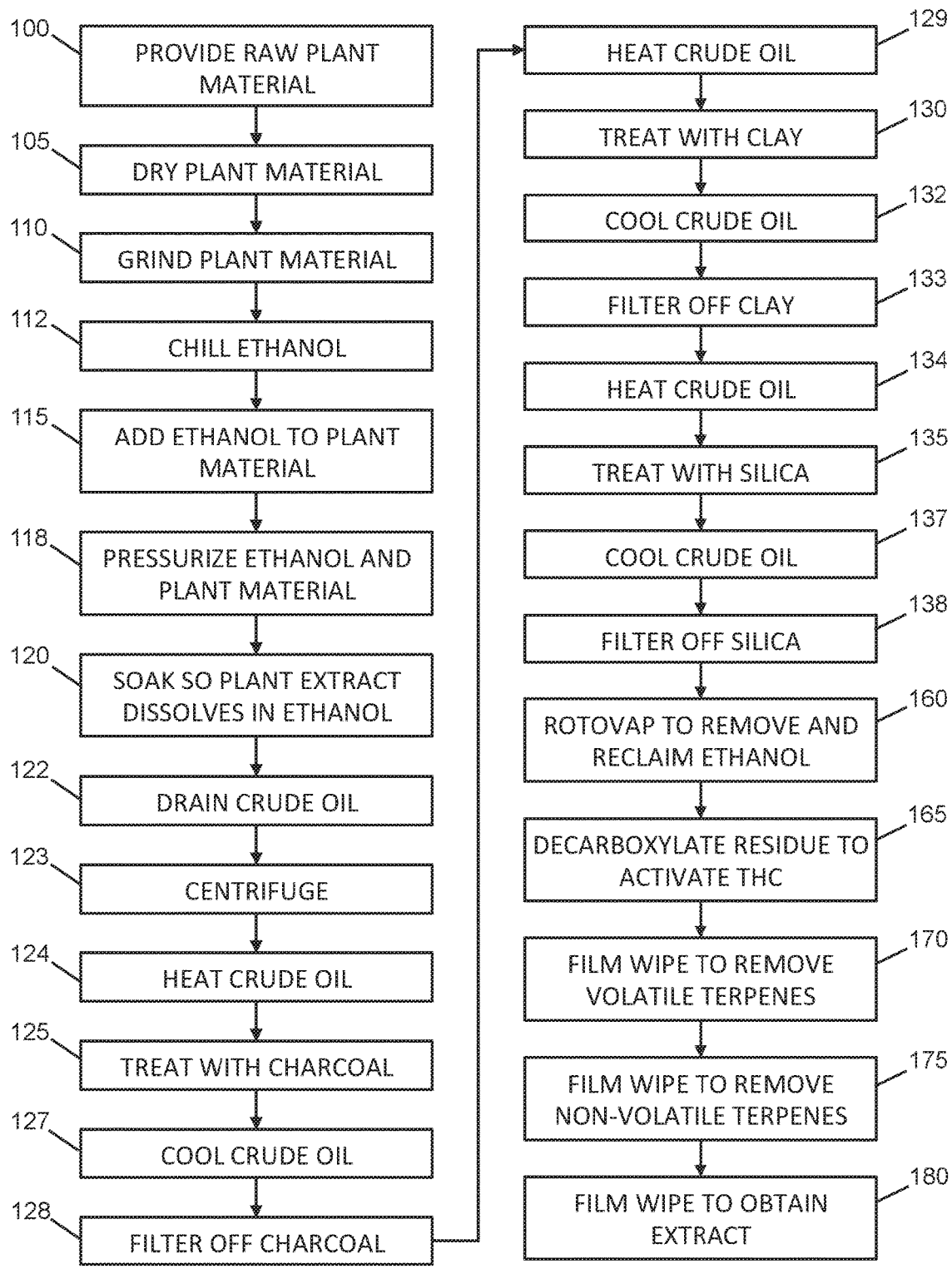
FIG. 2 is a flowchart showing more detailed steps of a process for extracting cannabinoids according to an embodiment of the present invention.

Referring to FIG. 2, a detailed process for the extraction of cannabinoids is shown. This exemplary process relates to the extraction of cannabinoids from cannabis plant material. Steps 100-123 relate to the primary extraction phase. Steps 124-138 relate to the adsorbent media treatment stage. The rotovap stage 160 forms the solvent reclamation phase. Step 165 relates to the decarboxylation stage, and steps 170-180 relate to the distillation of the cannabinoids.

In step 100, raw cannabis plant material is provided. The raw cannabis plant material includes, for example, the flower, the leaves and the stems close to the leaves. Any part of the plant that contains cannabinoid resin glands can be included. Not all stems and leaves have these glands present. In other cases, the raw cannabis plant material includes only the flowers, or the raw cannabis plant material includes only the leaves and stems, i.e. the parts of the plant that would normally be considered waste, in which valuable phytochemicals are found only in lower concentrations.

In step 105, the raw cannabis plant material is dried, if it is not already provided in dried form. The raw cannabis plant material is dried in a dry room with a dehumidifier air controller, or it may be flash dried in a vacuum oven at a pressure of <2 kPa. Ideally, the moisture content of the raw cannabis plant material after drying is 10% or below, by weight. The temperature of the oven and the drying time depend on how much moisture the raw material has, and how much raw material there is. Moisture content is measured using a moisture analyzer. In some embodiments a hygrometer may be used. The lower the moisture content is, the better, because lower moisture will cause less dilution of the ethanol than if the moisture level were higher. If the ethanol that is reclaimed is diluted with water, it will be less effective for repeat processes. Nevertheless, in other embodiments, the moisture content can be as high as 15% while still allowing for an acceptable process. In other embodiments, other drying techniques may be used.

In step 110, the dried plant material is ground, for example to an average size between 250-300 µm. However, it is possible in other embodiments to grind the dried plant material to a size of thousands of microns, and the process has been found to work with average particle sizes of up to 3000-5000 µm. If the plant material is ground to less than 250 µm, say, then problems occur with unwanted packing of the material in the material columns (240, FIG. 3). Notably, the unwanted packing is due to the raw material packing into a plug under applied pressure. If the particulate is too fine, the raw material will form a seemingly solid mass making it difficult for ethanol to pass through it.

Note that, in other embodiments, the grinding step may take place before the drying step.

In step 112, the ethanol is chilled to a temperature between −35° C. and −50° C., in a tank surrounded by a pressurized liquid $CO_2$ jacket, for example. In other embodiments, the ethanol is chilled using a heat exchanger or a jacket of solid $CO_2$ or liquid nitrogen.

In step 115, the chilled ethanol is added to the material column into which the ground and dried plant material has been placed. Typically, approximately 50 liters of ethanol is used for every 5 kg of plant material, although it is possible that other ratios can be used.

In some embodiments where the ethanol is chilled, the optimum temperature has been found to be −45° C. However, the optimum temperature may be different in other embodiments. The optimum choice is a compromise between keeping the time needed for chilling to a minimum, keeping the consumption of the liquid nitrogen and/or liquid $CO_2$ coolant down, and maximizing the miscibility of the ethanol with the cannabinoids that are to be extracted. Nevertheless, using the treatment and filtration process described herein, the fats and lipids can be removed economically from the extracted crude oil and ethanol mixture. The use of chilled ethanol is more efficient for the process in general with respect to post-filtration steps, however, it has slightly less efficiency with respect to yield. Non-chilled ethanol is more efficient in terms of extraction yield but very inefficient for post-filtration steps. Non-chilled ethanol extracts unwanted fats, waxes and lipids. In some embodiments, step 112 is optional and the extraction process takes place with the ethanol chilled or at room temperature, i.e. within a range of −60° C. to +18° C.

In step 118, the mixture of ethanol and plant material is pressurized to a pressure in the range of 70-280 kPa (10-40 psi). The aim is to select a pressure that is just low enough to prevent a plug of plant material forming within the material column. The actual value of the pressure is determined by the material column packing. The tighter the raw cannabis plant material is packed into the column, the lower is the upper pressure limit with which the ethanol can be driven through the column. While under pressure, the temperature of the mixture may vary by up to ±5° C., but it should not be allowed to rise above −35° C. Note that in some embodiments, pressure is applied to the mixture of ethanol and plant material by centrifugal action.

In step 120, the plant material is allowed to soak in the ethanol for a while in order to allow the cannabinoids to dissolve into it. Typically, the plant material soaks for up to 15 minutes provided that the temperature is below −35° C.

In other embodiments, the soaking time may be different. The pressure is maintained in the range of 70-280 kPa (10-40 psi) while the mixture of ethanol and plant material is soaking.

In step 122, the ethanol, now with the crude oil and dissolved cannabinoids, is drained off from the bulk of the plant material, to form a mixture of crude oil and ethanol. This mixture is the total fluid that comes directly out of the extractor (material column) post-extraction. The crude oil contains cannabinoids and other phyto-compounds, and is dissolved in the ethanol. The mixture also contains some unwanted residual plant matter and other undesirable components. The crude oil and ethanol mixture is drained off under a pressure in the range of 70-280 kPa (10-40 psi), i.e. it is the same pressure as the pressure used to soak the plant material. In other embodiments, a vacuum is used to drain the crude oil and ethanol mixture instead of the application of pressure.

In other embodiments, the ethanol is pumped continuously through the raw cannabis plant material under pressure in the range of 70-280 kPa (10-40 psi), without the specific soaking step.

Optionally, in step 123, a centrifuge is used to separate the further plant material from the crude oil and ethanol mixture. The centrifuge may be used instead of the step 122 of draining of the material column, or instead of the pumping of ethanol through the raw material under pressure. In this case the contents of the material column are transferred into the centrifuge directly, or into a mesh bag and then placed into the centrifuge.

In step 124, the crude oil and ethanol mixture is heated to a temperature between 60° C. and 78° C. for treatment with charcoal. It is important not to exceed the upper temperature of this range, because targeted elements in the crude oil will melt into the liquid state and will be unable to be filtered out. Also, the ethanol will boil and there may be cannabinoid degradation. In other embodiments it is possible to omit this step and perform the subsequent filtration steps at room temperature or even using the crude oil and ethanol mixture in its previously chilled state, or at another chilled temperature, e.g. as low as −40° C.

In the following steps, the crude oil and ethanol mixture is treated and filtered to remove further plant material that is unavoidably retained in the mixture during the draining step. Treatment and filtration remove fats, lipids, chlorophyll, waxes, heavy metals and other undesirable chemicals. Typically, there are 1-5 different media treatments. While filtration is almost always required, the filtration steps required are not necessarily as robust if the ethanol used in the primary extraction phase is chilled, compared to if the ethanol is non-chilled.

In step 125, the crude oil and ethanol mixture is treated with charcoal. The charcoal removes pigments, chlorophyll, heavy metals and particulates. Charcoal is used as the first treatment medium in order to remove as much pigment as possible. The charcoal, when in particulate form, is first added to the heated, room temperature or chilled crude oil and ethanol mixture and then the mixture is agitated. The average size of the charcoal particles is in the range 0.25-150 µm, although other sizes are possible in other embodiments.

The crude oil and ethanol mixture is then cooled, or allowed to cool to a temperature of between 10-50° C. in step 127. Any charcoal that is in the crude oil and ethanol mixture is removed by filtering it out using borosilicate glass filter paper, in step 128, particularly if it has been added to the crude oil and ethanol mixture during the treatment process. Filtering out the charcoal is done at a temperature of between 10-50° C. Other filter media or material, or a filter screen may be used instead. For example, the solution is filtered through a 10-30 µm paper filter or screen and then through an 0.25-1 µm paper filter or screen. In other embodiments, a different number of paper or screen filters can be used, and they can have different sizes. In another example, a filter cartridge is used, with a pore size of 0.2-1 µm.

In step 129, the crude oil and ethanol mixture is reheated to a temperature between 60° C. and 78° C. for further treatment. In other embodiments it is possible to omit this step and perform the subsequent treatment and filtration steps at room temperature or even using the crude oil and ethanol mixture in its previously chilled state, or at another chilled temperature, e.g. as low as −40° C.

In step 130, the crude oil and ethanol mixture is treated with an agulite clay, also known as fuller's earth clay, palygorskite, attapulgite, or bentonite. The clay primarily removes pigments. The clay, when in particulate form, is first added to the heated crude oil and ethanol mixture and then the mixture is agitated. The average size of the clay particles is in the range 0.25-150 µm, although other sizes are possible in other embodiments.

The crude oil and ethanol mixture is then cooled, or allowed to cool to a temperature of between 10-50° C. in step 132. Any clay that is in the crude oil and ethanol mixture is removed by filtering it out in step 133, using borosilicate glass filter paper, particularly if it has been added to the crude oil and ethanol mixture during the treatment process. Other filter media or material, or a filter screen may be used instead. For example, the solution is filtered through a 10-30 µm paper filter or screen and then through an 0.25-1 µm paper filter or screen. In other embodiments, a different number of paper or screen filters can be used, and they can have different sizes. In another example, a filter cartridge is used, with a pore size of 0.2-1 µm.

In step 134, the crude oil and ethanol mixture is reheated to a temperature between 60° C. and 78° C. for still further filtering. In other embodiments it is possible to omit this step and perform the subsequent treatment and filtration steps at room temperature or even using the crude oil and ethanol mixture in its previously chilled state, or at another chilled temperature, e.g. as low as −40° C.

In step 135, the crude oil and ethanol mixture is then treated with silica. The silica removes very fine plant matter and other particulates. The silica, when in particulate form, is first added to the heated crude oil and ethanol mixture and then the mixture is agitated. The average size of the silica particles is in the range 0.25-150 µm, although other sizes are possible in other embodiments. The removal very fine solid particulates helps the winterization of the oil to occur faster. Additionally, it allows for visibility of the product, which in turn allows one to review the integrity of the filtration process.

The crude oil and ethanol mixture is then cooled or allowed to cool to a temperature of between 10-50° C. in step 137. Any silica that is in the crude oil and ethanol mixture is removed by filtering it out in step 138, using borosilicate glass filter paper, particularly if it has been added to the crude oil and ethanol mixture during the treatment process. Other filter media or material, or a filter screen may be used instead. For example, the solution is filtered through a 10-30 µm paper filter or screen and then through an 0.25-1 µm paper filter or screen. In other embodiments, a different number of paper or screen filters can be used, and they can have different sizes. In another example, a filter cartridge is used, with a pore size of 0.2-1 µm.

In step 160, the resulting oil and ethanol mixture is then processed with a rotovap to remove and reclaim any ethanol that remains in it. The temperature of the rotovap is 43-49° C., and it is operated at a pressure of 83-101 kPa (25-30 inHg, 635-760 mmHg). Other evaporators may be used in other embodiments. The ethanol that is reclaimed can be used to extract cannabinoids from a further batch of dried and ground raw cannabis plant material.

After the remaining ethanol has been removed using the rotovap, decarboxylation is performed on the resulting oil in step 165. The oil is heated to 120-140° C. in order to evaporate residual solvents and to convert THCa into THC, releasing $CO_2$ in the process. If the temperature is below this range, then potentially there will be some residual ethanol. The majority of the $CO_2$ that is produced from decarboxylation is removed in order to ensure consistent vacuum levels later on in the process. If the temperature is above this range, then product degradation occurs. The oil is warmed up gradually while stirring so as not to overheat portions of it. In the decarboxylation step the residual ethanol is not reclaimed. The decarboxylation process typically takes several hours. Note that in an embodiment described below, the decarboxylation step is not performed in a rotovap, but in a wiped film under vacuum, to lower the required contact temperatures and prevent oxidation.

Figure 3:
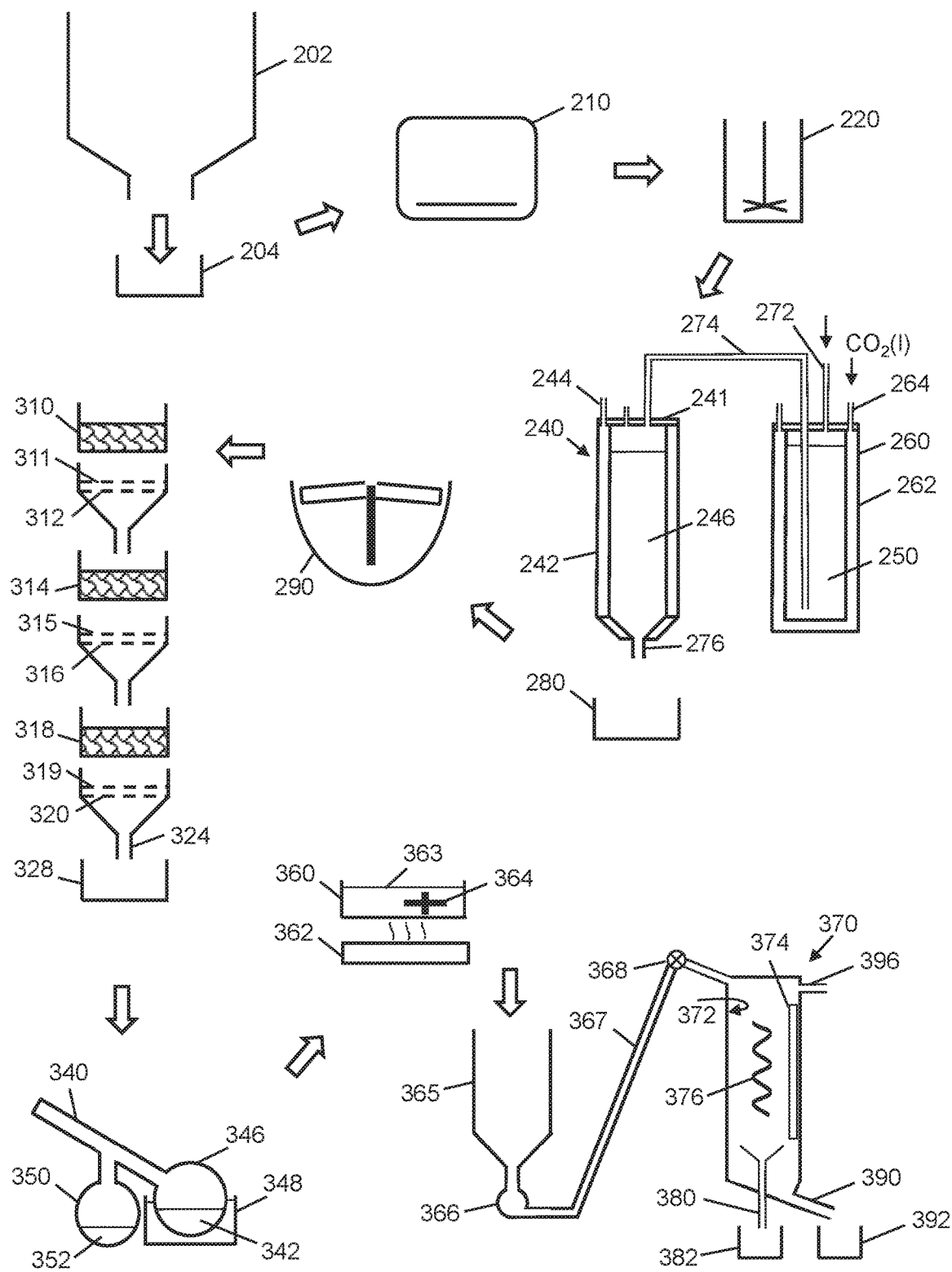
FIG. 3 is a schematic diagram of the apparatus used for the extraction of cannabinoids according to an embodiment of the present invention.

In step 170 and referring to FIG. 3, the decarboxylated oil is run through a short-path distillation film wipe apparatus 370. Since we are using a wiped film distillation process versus a conventional short path still apparatus it is important to have separated the waxes, fats and lipids pre-distillation. If this is not done, the waxes, fats and lipids will be wiped onto the wipe film causing the distillation of some of these elements into the final product.

The decarboxylated oil is first run through the short-path distillation film wipe apparatus to remove some volatile terpenes. The temperature of the feed tank 365 to the film wipe is set in the range 100-115° C., and is more usually set in the range 107-110° C. The temperatures of the pump 366 and feed line 367 to the film wipe are set at the same value as the feed tank. The temperature of the residue discharge arm 390 and its associated pump, not shown, is also set in the range 100-115° C., and is also more usually set in the range 107-110° C. The temperature of the target heater, which controls the temperature of the inner wall 372, is set within a range of 155-162° C., usually 159.5° C. The condensing coil 376 is set at a temperature of 58° C., as is the target or distillate discharge arm 380 and its associated pump (not shown). A further temperature control unit maintains the temperature of a cold trap between the vacuum port 396 and the vacuum pump at −22 to −30° C., although even cooler temperatures are possible. The film-wipe process is performed at a pressure of 0.3-0.8 mbar, or lower.

In step 175, the residual oil, after volatile terpene removal, is re-run through the short-path distillation film wipe to remove some non-volatile terpenes. All of the temperatures are the same except for the temperature of the inner wall, which is typically set to a higher temperature and is in the range 159-162° C. The pressure is the same, at 0.3-0.8 mbar, or lower.

In step 180, the further residual oil is again run through the short-path distillation film wipe to remove the cannabinoids as a whole. The temperature of the feed tank 365 to the film wipe is set in the range 100-115° C., and is more usually set in the range 107-110° C. The temperatures of the pump 366 and feed line 367 to the film wipe are set at the same value as the feed tank. The temperature of the residue discharge arm 390 and its associated pump, not shown, is also set in the range 100-115° C., and is also more usually set in the range 107-110° C. The temperature of the target heater, which controls the temperature of the inner wall 372, is set within a range of 168.5-170° C. The condensing coil 376 is set at a temperature of 74° C., as is the target or distillate discharge arm 380 and its associated pump (not shown). The temperature of the cold trap between the vacuum port 396 and the vacuum pump is −22 to −30° C., although even cooler temperatures are possible. The film-wipe process is performed at a pressure of 0.03-0.08 mbar, or lower.

The result from the distillate discharge arm is a tasteless, odourless oil that contains up to 99% pure cannabinoids. Often, however, the further residual oil will require another pass through the wiped-film apparatus in order to achieve purities of 90% and over.

Using this process, a given weight of dried cannabis can be turned into very approximately 10-15% crude oil, which yields anywhere from 4-10% pure cannabinoids, again very approximately.

D. Apparatus

Referring to FIG. 3, an example of the apparatus is shown schematically. Raw cannabis plant material is provided in a hopper 202, for example, and is released in batches into container 204. The raw cannabis plant material is dried in vacuum oven 210. Next, the dried plant material is placed into a grinder 220. After the grinding step, the ground plant material is placed into one or more material columns 240. Each column has a lid 241 that is removable so that the ground plant material can be placed into it. Each column holds 1.5-4.5 kg (3-10 lb) of plant material depending on its size. Other capacities are also possible. In one example apparatus, there are four material columns 240. The material column may be surrounded by an insulating wall or vacuum jacket 242, which can be evacuated via port 244. Alternately, an insulating jacket may be wrapped around the material column. The insulating wall 242 or jacket helps to maintain the contents 246 cool in the process that uses chilled ethanol as the solvent. When using chilled ethanol, the material column is maintained chilled by the use of pressurized, liquid $CO_2$ in the jacket. The ethanol 250 is cooled in a cryogenic tank 260, the inner temperature of which is maintained low by a jacket 262 filled with pressurized liquid $CO_2$ via port 264. In other embodiments, other refrigerants can be used, or a chiller or heat exchanger can be used.

Pressurized nitrogen gas is fed into the port 272, forcing the chilled ethanol 250 through insulated tube 274 into the material column 240. The pressure of the nitrogen is used to maintain the pressure of the mixture 246 of ethanol and raw cannabis plant material, and/or to pump the ethanol through the raw cannabis plant material. After the raw cannabis plant material has soaked in the ethanol, the ethanol, now with dissolved cannabinoids, is drained out of the material column 240 as a mixture of crude oil and ethanol, via outlet pipe 276 into container 280. The bulk of the raw cannabis plant material remains in the material column 240. The crude oil and ethanol mixture may alternately be pumped out of the material column under the pressure of the nitrogen.

Optionally, a centrifuge 290 is used to separate the bulk of the plant material from the mixture. If the centrifuge 290 is used, the contents of the material column are emptied into the centrifuge, which then separates the bulk of the plant material from the crude oil and ethanol mixture. The centrifuge 290 may be used instead of the draining of the material column, or instead of the pumping of ethanol through the raw material under pressure, or it may be used as well as the draining and/or pumping steps.

The crude oil and ethanol mixture is then treated with various media and fed into multiple different filters sequentially. In this embodiment, the first treatment unit is charcoal 310. Below the charcoal there is a 10-30 µm filter 311 and an 0.25-1 µm filter 312 for filtering out charcoal. Next there is a clay treatment unit 314, below which is a 10-30 µm filter 315 and an 0.25-1 µm filter 316 for filtering out the clay. Following this is a silica treatment 318, below which is a 10-30 µm filter 319 and an 0.25-1 µm filter 320 for filtering out the silica. Each of the filters can be independently replaced. After filtration, the resulting oil and ethanol mixture leaves the final filter via exit pipe 324 and is collected in container 328.

The filtered oil and ethanol mixture is then passed into a rotovap 340. The oil and ethanol mixture 342 is maintained at an elevated temperature in flask 346, which is heated in a temperature bath 348. Flask 350 collects the ethanol 352, which is evaporated from the oil and ethanol mixture 342.

After the ethanol 352 has been reclaimed from the oil 342, the oil is decarboxylated in container 360, which is heated by heater 362. During the decarboxylation process, the oil 363 is stirred by a magnetic stirrer 364. After decarboxylation, the oil 363 is transferred to a feed chamber 365. At the bottom of the feed chamber 365, a pump 366 pumps the oil via a feed line 367 and a check valve 368 into a short-path film wipe apparatus 370. Pump rates are typically 1000-1500 ml/hr, and depend on the $CO_2$ being given off, if any, the percentage of THCa converted to THC, and the vacuum pressure of the short-path film wipe apparatus. In the short-path film wipe apparatus 370, the oil is wiped in a thin film around the heated, inside wall 372 of the film wipe apparatus 370 by a blade 374. The inside wall 372 is heated via a temperature-maintained jacket. A cooler, condensing coil 376 condenses the target fraction, which leaves the film wipe apparatus 370 as a distillate via target discharge tube 380 and is collected in container 382. The residual liquids fall down the inside wall 372 of the film wipe 370 and exit through residual arm 390 to be collected in container 392. The film wiping occurs under reduced pressure provided by a vacuum pump connected to port 396 via a cold trap.

E. Further Exemplary Process

Figure 4:
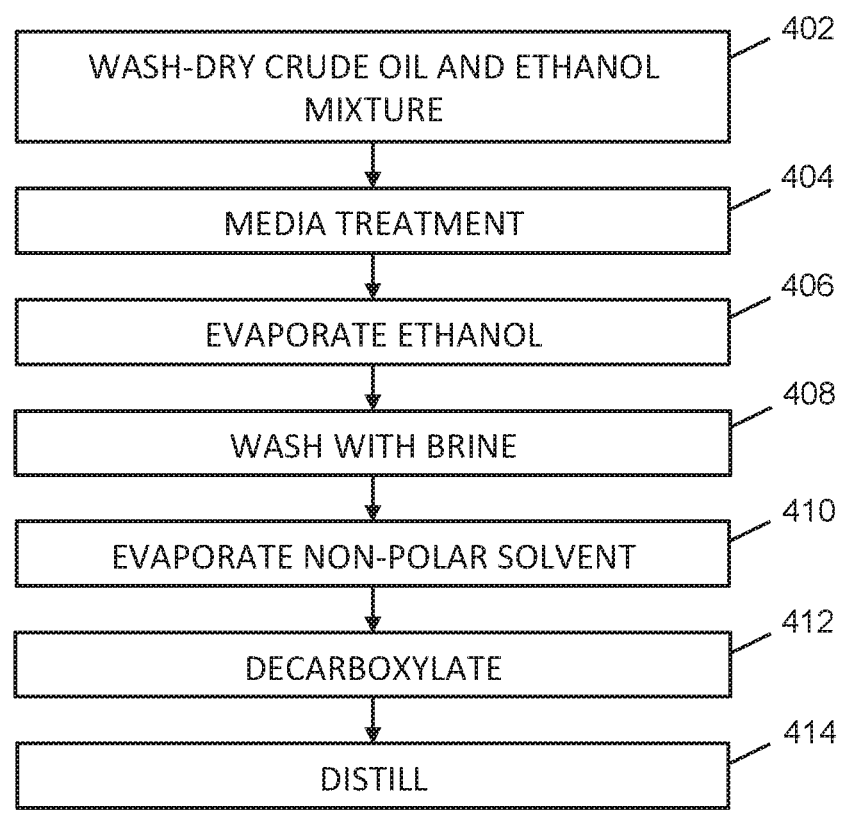
FIG. 4 is a high-level flowchart showing the key steps of a process for extracting cannabinoids according to a further embodiment of the present invention.

Referring to FIG. 4, a flowchart summarizing the basic steps of an alternate process is shown.

In step 402, after adding ethanol to a WSD separator containing the raw cannabis plant material, the plant material is washed with the ethanol in the WSD. The raw cannabis plant material is then "dried" using the spinning cycle function of the WSD separator. Then, in step 404, the resulting crude oil and ethanol mixture is treated with different media and filtered. During step 404, impurities contained in the crude oil and ethanol mixture are removed. In step 406, the ethanol from the resulting oil and ethanol mixture is evaporated and reclaimed. After that, in step 408, the oil is washed with a brine solution and then the non-polar solvent added prior to the brine wash is removed in step 410. Steps 406 and 410 are considered to be the solvent reclamation stages.

In step 412, the oil remaining after the evaporation of the non-polar solvent is decarboxylated to activate the THC and evaporate any remaining solvent. The residue after decarboxylation is then, in step 414, distilled using a film wipe apparatus 592 in order to extract the cannabinoids.

Figure 5:
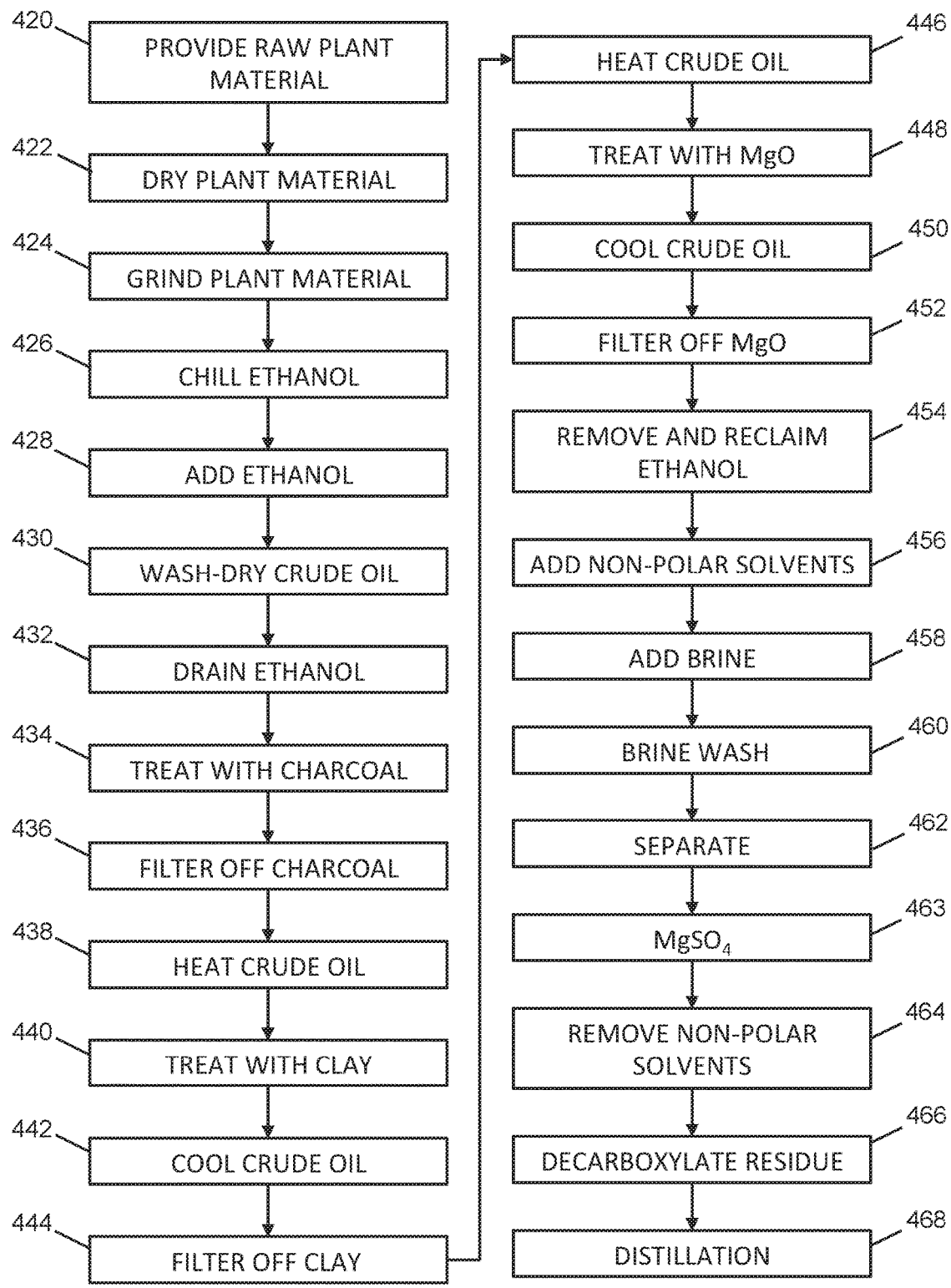
FIG. 5 is a flowchart showing more detailed steps of a process for extracting cannabinoids according to a further embodiment of the present invention.

Referring to FIG. 5, details of the alternate process for the extraction of cannabinoids are shown. Steps 420-432 relate to the primary extraction phase. Steps 434-452 relate to the media treatment and filtration stage. The remove and reclaim ethanol stage 454 and the non-polar solvent removal stage 464 form the solvent reclamation phases. Steps 456-463 are the brine washing stage. Step 466 relates to the decarboxylation stage, and step 468 relates to the distillation of the cannabinoids.

In step 420, raw cannabis plant material is provided. In step 422, the raw cannabis plant material is dried, if it is not already provided in dried form. Ideally, the moisture content of the raw cannabis plant material after drying is 10% or below, by weight. In other embodiments, the moisture content can be as high as 15% while still allowing for an acceptable process. In other embodiments, other drying techniques may be used.

In step 424, the dried plant material is ground, for example to an average size between 250-300 µm. However, it is possible in other embodiments to grind the dried plant material to a size of thousands of microns, and the process has been found to work with average particle sizes of up to 3000-9000 µm. Note that, in other embodiments, the grinding step may take place before the drying step. The ground and dried plant material is then placed in a closed, porous bag.

In step 426, the ethanol is chilled (if necessary) to a temperature between −60° C. and +18° C., in a tank surrounded by a pressurized liquid $CO_2$ jacket, for example. In some embodiments, the ethanol is used at room temperature, i.e. 18° C. However, chilled ethanol, when used for extraction, reduces impurities like fats, lipids and pigments in the crude cannabis oil.

In step 428, the chilled ethanol is added to the WSD separator into which the bag of ground and dried plant material has been placed. Typically, approximately 40-50 liters of chilled ethanol are used for every 5-6 kg of plant material (i.e. 6.6-10 liters per kg), although it is possible that other ratios can be used. In step 430, the plant material and ethanol mixture is run through the wash and spin modes of the WSD separator. The ethanol is continuously fed into the drum as it is spun. Depending on the embodiment, the drum is spun for 8-15 minutes. The ethanol, in some embodiments, is pressurized to between 1-15 psi (7-100 kPa) as is it fed into the drum. Due to the centrifugal force, the crude oil is extracted (i.e. dissolved into the ethanol). The extent of the drying, i.e. removal of liquid from the plant material, depends on the speed of the spin cycle. The WSD separator has a centrifuge drum for the wash and extraction, and a spin cycle mode to separate off the solvent. In step 432, the ethanol, now with dissolved extracts (i.e. a crude oil and ethanol mixture), is drained out of the centrifuge drum during the spin cycle mode. The crude oil and ethanol mixture is drained off as a result of the centrifugal force due to the spinning action of the drum. The solid plant material remains inside the mesh bag.

In some embodiments where the ethanol is chilled, the optimum temperature has been found to be −45° C. However, the optimum temperature may be different in other embodiments.

In the following steps, the crude oil and ethanol mixture is treated with different media and filtered to remove chlorophyll, pigments, plant material and any other impurities that are unavoidably retained in the mixture after the draining step 432. Typically, there are 1-5 different treatment media.

In step 434, the crude oil and ethanol mixture is treated with charcoal (charcoal scrub). The crude oil and ethanol mixture is at a temperature between −10° C. and +85° C. for the charcoal scrub. The charcoal, when in particulate form, is first added to the crude oil and ethanol mixture and then the mixture is agitated. The average size of the charcoal particles is in the range 0.25-150 μm, although other sizes are possible in other embodiments.

Any charcoal that is in the crude oil and ethanol mixture is removed by filtering it out using lenticular depth filtration apparatuses and/or column housing filters with insert cartridges, in step 436. Lenticular depth filtration systems usually use lenticular shaped filters that are able to retain and collect the charcoal particles. A filter cartridge with a pore size of 0.2-1 μm is used. Filtering out the charcoal is done at a temperature between −10° C. and 50° C.

In another embodiment, lenticular filtration alone for the charcoal treatment is used to take care of both the charcoal treatment and the filtration process simultaneously.

In step 438, the crude oil and ethanol mixture is reheated to a temperature between 60° C. and 78° C. for further treatment. In other embodiments it is possible to omit this step and perform the subsequent treatment and filtration steps at room temperature or even using the crude oil and ethanol mixture in its previously chilled state, or at another chilled temperature, e.g. as low as −40° C.

In step 440, the crude oil and ethanol mixture is treated with a bentonite clay. The clay, when in particulate form, is first added to the heated crude oil and ethanol mixture and then the mixture is agitated. The average size of the clay particles is in the range 0.25-150 μm, although other sizes are possible in other embodiments.

The crude oil and ethanol mixture is then allowed to cool to a temperature of between 10-50° C. in step 442. Any clay that is in the crude oil and ethanol mixture is removed by filtering it out in step 444 using lenticular depth filtration apparatuses and/or column housing filters with insert cartridges. A filter cartridge with a pore size of 0.2-1 μm is used.

In step 446, the crude oil and ethanol mixture is reheated to a temperature between 60° C. and 78° C. for still further treatment. In other embodiments it is possible to omit this step and perform the subsequent treatment and filtration steps at room temperature or even using the crude oil and ethanol mixture in its previously chilled state, or at another chilled temperature, e.g. as low as −40° C.

In step 448, the crude oil and ethanol mixture is then treated with magnesium oxide. The magnesium oxide, in particulate form, is first added to the heated crude oil and ethanol mixture and then the mixture is agitated. The average size of the magnesium oxide particles is in the range 0.25-150 μm, although other sizes are possible in other embodiments.

The crude oil and ethanol mixture is then allowed to cool to a temperature of between 10-50° C. in step 450. Any magnesium oxide that is in the crude oil and ethanol mixture is removed by filtering it out in step 452, using lenticular depth filtration apparatuses and/or column housing filters with insert cartridges.

In one embodiment, the filtering off of the charcoal (step 436), the clay (step 444) and the MgO (step 452) are all performed as a single step after the treatment with MgO.

In a further embodiment, a silica gel is used as a media treatment, after the clay treatment and before the MgO treatment.

In step 454, the resulting oil and ethanol mixture is then processed with a rotovap to remove and reclaim the ethanol from the mixture. The temperature of the rotovap is 43-49° C., and it is operated at a pressure of 83-101 kPa (25-30 inHg, 635-760 mmHg). Other evaporators or evaporation techniques may be used in other embodiments, for example falling film evaporators, rising film evaporators or flash or spray dryers can be used. The ethanol that is reclaimed may be used to extract cannabinoids from a further batch of dried and ground raw cannabis plant material. Typically, 75% of the ethanol used is reclaimed.

The oil, now without ethanol, is then mixed with hexane, heptane or pentane (non-polar solvents) with the mixing ratio of hexane, heptane or pentane to oil of 1:1 in step 456 to result in an oil and solvent mixture. Note that other ratios are also possible. The role of non-polar solvents here is to further extract the oil for following processing steps, due to their ability to solubilize cannabinoids. Non-polar solvents such as hexane, heptane or pentane dissolve fats and oils and leave behind proteins, carbohydrates and other impurities insoluble in these solvents and other non-polar solvents. This type of solvent is also used in the oil extraction field for its ability to be removed due to its low boiling point. In addition to that, non-polar solvents exhibit the property of being insoluble in water, which helps to a certain extent to separate water and other water-solubles from the non-polar solvent.

Next, the brine solution is added to the oil and solvent mixture in step 458. The oil and solvent mixture is then washed with brine (60% to 100% saturated in salt) to remove water-soluble compounds in step 460, and to remove impurities and any traces of the treatment media that may have remained in the oil. Brine helps to disrupt emulsions and dry the oil by extracting water that may have dissolved in the mixture, and also extracts ethanol from the non-polar phase and crude oil into the brine solution. Afterwards the brine solution is separated from the oil in step 462.

The brine solution is prepared with distilled water and kosher salt, i.e. iodine-free sodium chloride. After brine-washing, the brine, with water-soluble compounds, is separated from the oil and non-polar solvent by means of a centrifuge or a gravity fed separatory funnel. Unless 99.9999% purity solvents are used, there is always a water content that extracts solubles (i.e. sugars) from the raw cannabis plant material in the primary extraction stage. These water-soluble compounds need to be removed through a liquid to liquid extraction brine wash.

As an example, 500 ml of hexane, pentane or heptane is added to 500 ml of oil and then homogenized by means of an overhead stirrer. Then, 1000 ml of distilled water saturated with kosher sodium chloride at 60-100% saturation is added to the oil and solvent mixture (i.e. the ratio of non-polar solvent to oil to brine is 1:1:2) and agitated for 5 to 30 min with an overhead stirrer.

After the brine has been removed from the oil, the remaining traces of water, if any, are then removed from the oil with a magnesium sulfate treatment, in step 463, in which powdered $MgSO_4$ is swirled around in the oil and then filtered off, e.g. by gravity filtration.

In step 464, the oil and solvent mixture is then processed with a rotovap to remove and reclaim the non-polar solvent. The temperature of the rotovap is 43-49° C., and it is operated at a pressure of 83-101 kPa (25-30 inHg, 635-760 mmHg). The non-polar solvent such as hexane, heptane and/or pentane that is reclaimed may be used for future brine wash applications. About 75% of the non-polar solvent is reclaimed for further use.

After the non-polar solvent has been removed using the rotovap, decarboxylation is performed on the resulting oil in step 466. Decarboxylation is carried out to convert THCa into THC, releasing $CO_2$ in the process. In the process, residual solvents that may be present are evaporated off.

In one embodiment, the oil is first run through a short-path distillation film wipe apparatus 592 to convert THCa to THC. The temperature of the feed tank 584 (FIG. 6B) to the film wipe is set in the range 100-115° C. The temperatures of the pump 586 and feed line 588 to the film wipe apparatus 592 are set at the same value as the feed tank 584. The temperature of the residue discharge arm 604 and its associated pump, not shown, is also set in the range 100-115° C., and is also more usually set in the range 107-110° C. The temperature of the target heater, which controls the temperature of the inner wall 594, is set within a range of 140-175° C., usually 170° C.

The temperature of the inner wall is controlled by setting the temperature of a bath 595. A pump then circulates fluid that is heated to the bath temperature through a jacket around the outside of the wall. As such, it is to be expected that the inner wall temperature is slightly below that of the bath temperature, depending on, for example, the temperature and rate at which the oil is wiped onto the inner wall 594. Other temperatures of the film wipe apparatus are set in a similar way. These other temperatures are also expected to be slightly different to the bath setting, but not to a significant level. The condensing coil 598 is set at a temperature of 0° C. to -20° C., as is the target or distillate discharge arm 600 and its associated pump (not shown).

Liquid nitrogen is used to maintain cryogenic temperatures in a cold trap between the vacuum port 608 and the vacuum pump (not shown) of -180° C. to -196° C. Use of these temperatures allows for a deep vacuum to be maintained. The film-wipe process is performed at a pressure of 150-200 mbar. The decarboxylated oil is collected via the distillate arm.

While the film wipe temperature is higher than the minimum 90° C. required for THCa conversion under vacuum, and in the range where product degradation may occur, the dwell time at these elevated temperatures in the film is low enough that insignificant amounts of product degradation occur. Also, the temperature settings do not actually represent the contact temperature, as the settings are set on the circulation bath fluid and do not represent the temperature of the oil that is in contact with the glass surface area of the evaporator. The glass acts as an insulator between the heat transfer fluid and the oil. The temperature difference between the heat transfer fluid from the bath and the heated oil is expected to be in the range of 1-5° C.

Decarboxylation is performed under vacuum to lower the temperature required to convert the THCa to THC. It can either be done in the film wipe apparatus 592 effectively as a decarboxylation pass or done in a heated reactor (e.g. 504), for example. The oil itself needs to reach temperatures of at least 105° C. at atmospheric pressure. If a vacuum reactor is used the oil needs only to be heated to at least 90° C. The same temperature (90° C.) may also be used when the film wipe apparatus 592 is used. The film wipe decarboxylation process allows for a much lower heat residence time so that degradation of the oil is lower when compared to decarboxylating in a reactor.

In other embodiments, decarboxylation is carried out by heating the oil to 90-110° C. under vacuum in an oven. If the temperature is below this range, then potentially there will be some residual solvent. The majority of the $CO_2$ that is produced from decarboxylation is removed in order to ensure consistent vacuum levels later on in the process. If the temperature is above this range, then product degradation occurs. This method of decarboxylation process typically takes several hours.

There are other ways in which the decarboxylation process can be carried out. For example, the cannabis resin is heated while on the plant biomass in ovens similar to the vacuum ovens used to dry the cannabis plant, prior to adding the ethanol for primary extraction. The process is to simply heat the biomass to 90° C. for a period of time subject to the quantity of biomass being heated.

The decarboxylated oil is run through the short-path distillation film wipe apparatus 592 once again, this time to remove some volatile terpenes. The temperature of the feed tank 584 to the film wipe 592 is set in the range 100-115° C., and is more usually set in the range 107-110° C. The temperatures of the pump 586 and feed line 588 to the film wipe 592 are set at the same value as the feed tank 584. The temperature of the residue discharge arm 604 and its associated pump, not shown, is also set in the range 100-115° C., and is also more usually set in the range 107-110° C. The temperature of the target heater, which controls the temperature of the inner wall 594, is set within a range of 140-145° C., usually 145° C. The condensing coil 598 is set at a temperature of 0 to -20° C., as is the target or distillate discharge arm 600 and its associated pump (not shown), via which the terpenes are removed. Liquid nitrogen is used to maintain cryogenic temperatures of a cold trap between the vacuum port 608 and the vacuum pump at -180 to -196° C. This film-wipe process is performed at a pressure of 0.001-0.01 mbar.

The residual oil from the preceding film wipe step is again run through the short-path distillation film wipe apparatus 592 to remove some non-volatile terpenes. Mostly volatile terpenes are removed in the prior step and mostly non-volatile terpenes removed in this step, as there is no sharp cut-off between volatile and non-volatile terpenes. The temperature of the feed tank 584 to the film wipe is set in the range 100-115° C., and is more usually set in the range 107-110° C. The temperatures of the pump 586 and feed line 588 to the film wipe 592 are set at the same value as the feed tank 584. The temperature of the residue discharge arm 604 and its associated pump, not shown, is also set in the range 100-115° C., and is also more usually set in the range 107-110° C. The temperature of the target heater, which controls the temperature of the inner wall 594, is set within a range of 145-159° C., usually 155° C. The condensing coil 598 is set at a temperature of 20 to 60° C., as is the target or distillate discharge arm 600 and its associated pump (not shown), via which the terpenes are removed. Liquid nitrogen is used to maintain cryogenic temperatures of a cold trap between the vacuum port 608 and the vacuum pump at -180 to -196° C. Use of the cryogenic temperatures allows for a deeper vacuum to be maintained. This film-wipe process is performed at a pressure of 0.001-0.01 mbar.

The residual oil from the preceding film wipe step is again run through the short-path distillation film wipe apparatus 592 to remove the cannabinoids as a whole. The temperature of the feed tank 584 to the film wipe is set in the range 100-115° C., and is more usually set in the range 107-110° C. The temperatures of the pump 586 and feed line 588 to the film wipe 592 are set at the same value as the feed tank 584. The temperature of the residue discharge arm 604 and its associated pump, not shown, is also set in the range 100-115° C., and is also more usually set in the range 107-110° C. The temperature of the target heater, which controls the temperature of the inner wall 594, is set within a range of 140-165° C. The condensing coil 598 is set at a temperature of 68-73° C., as is the target or distillate discharge arm 600 and its associated pump (not shown), via which the cannabinoids are removed. Liquid nitrogen is used to maintain cryogenic temperatures of a cold trap between the vacuum port 608 and the vacuum pump at −180 to −196° C. The film-wipe process is performed at a pressure of 0.0008-0.003 mbar. This pass requires the use of a diffusion pump to assist with achieving deeper vacuums. It is installed on the film wipe apparatus 592 but not used for the decarboxylation and terpene fraction passes.

The result from the distillate discharge arm 600 is a tasteless, odorless oil that contains up to 99% pure cannabinoids. Often, however, the resulting oil will require another pass through the wiped-film apparatus 592 in order to achieve purities of 90% and over.

F. Further Apparatus

Figure 6A:
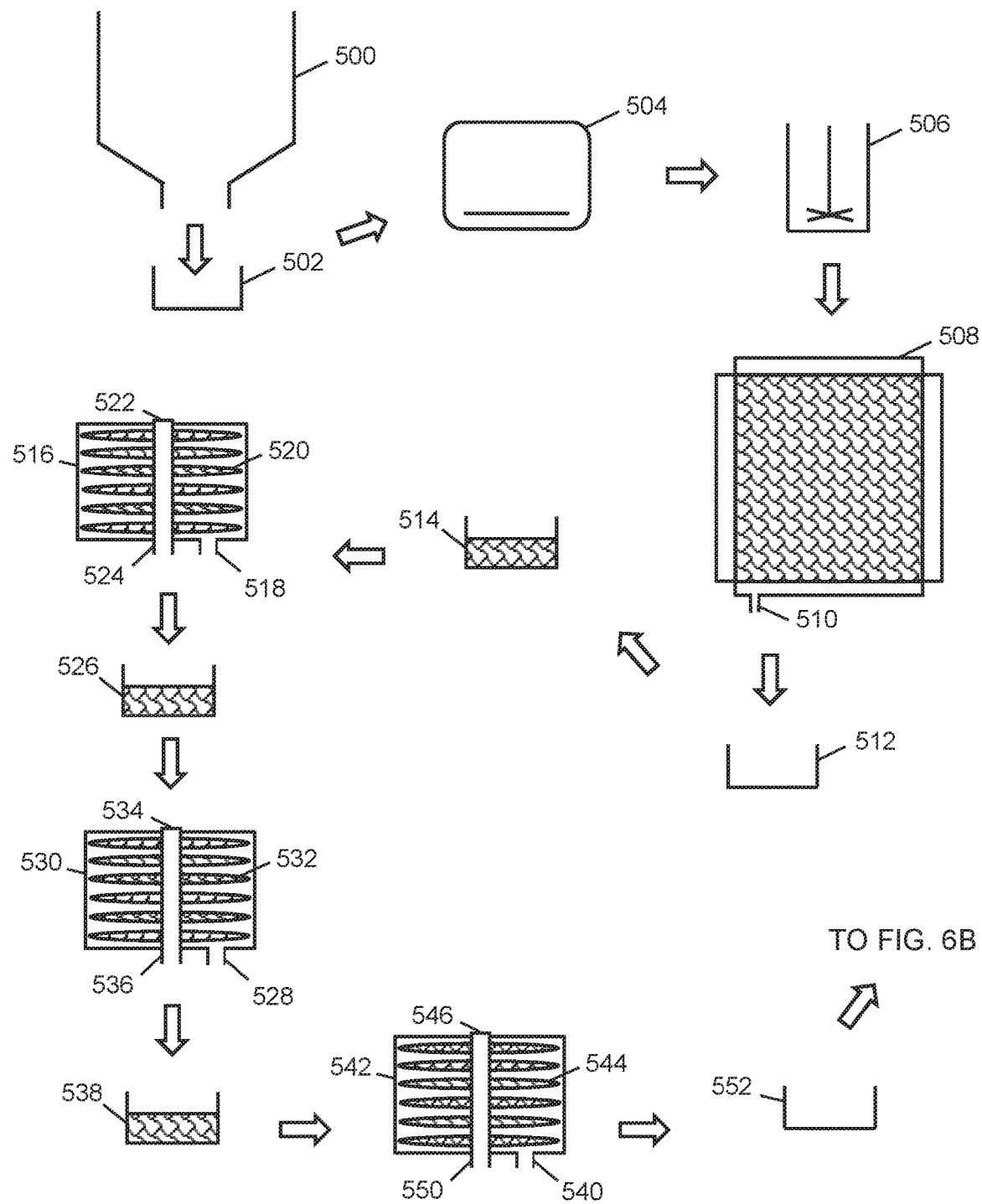
FIGS. 6A-B show a schematic diagram of the apparatus used for the extraction of cannabinoids according to a further embodiment of the present invention.
Figure 6B:
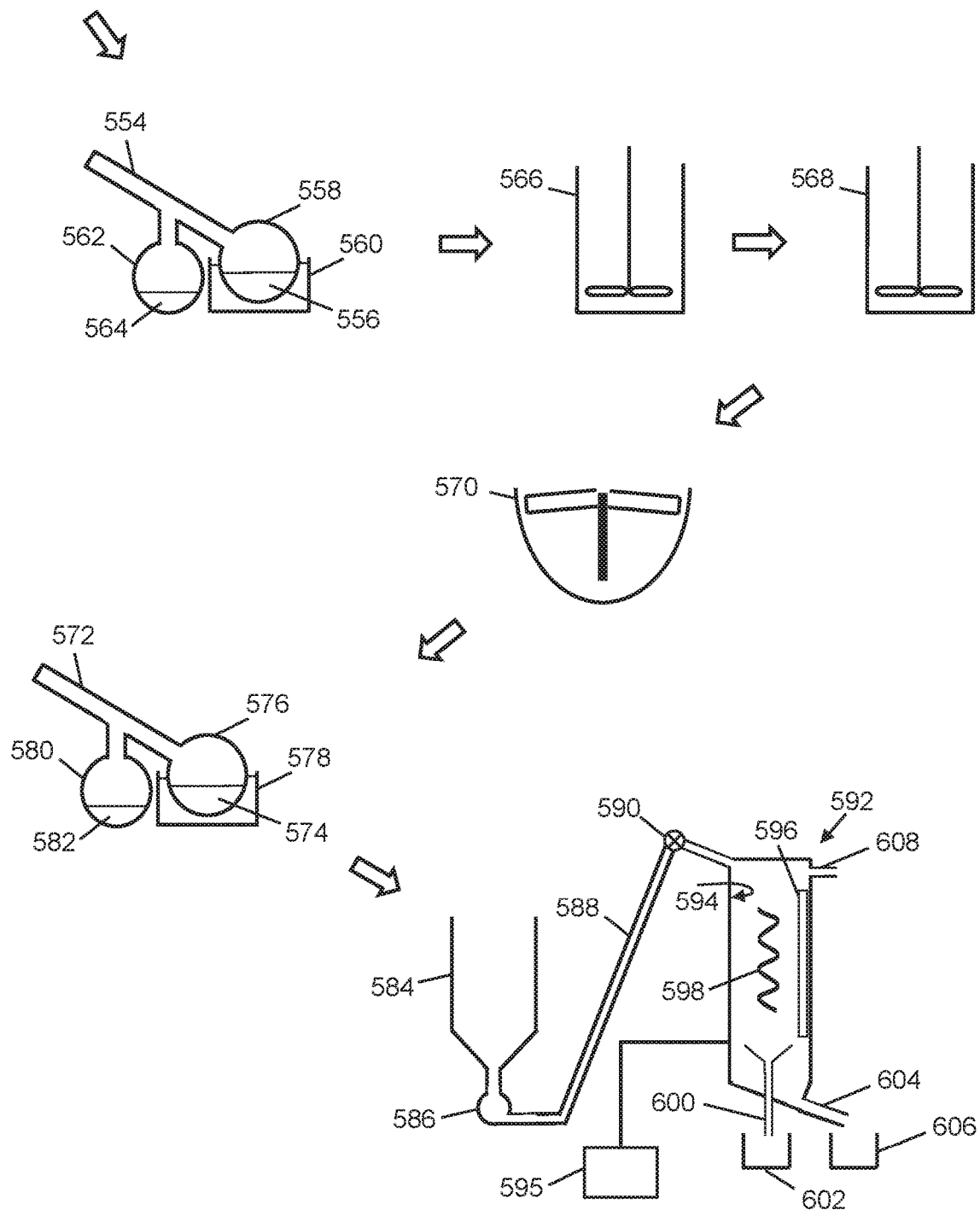

Referring to FIGS. 6A-B, an example of the apparatus for the further exemplary process is shown schematically.

Raw cannabis plant material is provided in a hopper 500, for example, and is released in batches into container 502. The raw cannabis plant material is dried in vacuum oven 504. Next, the dried plant material is placed into a grinder 506.

After the grinding step, in one embodiment, the ground plant material is placed into a bag in one or more WSD separator units 508.

After the raw cannabis plant material has been processed in the ethanol, the ethanol, now with dissolved cannabinoids, is drained out of the WSD separator 508 as a mixture of crude oil and ethanol, via outlet pipe 510 into container 512. An example extraction vessel holds 5-5.5 kgs of biomass in a single biomass cavity. Other capacities are also possible. The vessel is surrounded by an insulating jacket.

The crude oil and ethanol mixture is then fed into a charcoal treatment unit 514 and after being processed is then fed into a lenticular depth filtration apparatus 516 via an inlet pipe 518. The crude oil and ethanol mixture is filtered through one or more lenticular depth filtration cartridges 520. The lenticular depth filtration cartridges 520 retain the particles present in the crude oil and ethanol mixture within its structure. The crude oil and ethanol mixture is further carried into the central column 522 of the lenticular depth filtration apparatus 516 and collected through an outlet pipe 524 in a container with a bentonite clay treatment media 526.

After processing with charcoal, the crude oil and ethanol mixture is drained from the bentonite clay and then fed through inlet pipe 528 into a further lenticular depth filtration apparatus 530. The crude oil and ethanol mixture is then filtered through one or more lenticular depth filtration cartridges 532. The crude oil and ethanol mixture is further carried into a central column 534 of the lenticular depth filtration apparatus 530 and collected through an outlet pipe 536 into a container with a magnesium oxide treatment media 538.

The crude oil and ethanol mixture is drained from the magnesium oxide and then fed via an inlet pipe 540 into another lenticular depth filtration apparatus 542. The crude oil and ethanol mixture is then filtered through one or more lenticular depth filtration cartridges 544. The crude oil and ethanol mixture is further carried into a central column 546 of the lenticular depth filtration apparatus 542 and then through an outlet pipe 550 into a container 552.

Each of the filter cartridges can be independently replaced. Further treatment media and filter groups are used for additional treatment media in other embodiments.

The resulting oil and ethanol mixture is then passed into a rotovap 554. The oil and ethanol mixture 556 is maintained at an elevated temperature in flask 558, which is heated in a temperature bath 560. Flask 562 collects the ethanol 564, which is evaporated from the oil and ethanol mixture 556.

Hexane, heptane or pentane is then added to the oil and ethanol mixture with a mixing ratio of 1:1, to form an oil and solvent mixture, which is stirred with an overhead stirrer 566. The brine solution is added to the solution of oil/solvents and homogenized by means of an overhead stirrer 568. The water (as brine) is then separated from the mixture of brine/oil/solvent by means of a mechanical centrifuge 570.

The oil and solvent mixture is then passed into a rotovap 572. The oil and solvent mixture 574 is maintained at an elevated temperature in flask 576, which is heated in a temperature bath 578. Flask 580 collects the solvent 582, which is evaporated from the oil and solvent mixture 574.

After the solvents 582 have been reclaimed from the oil 574, the oil is decarboxylated. In one embodiment, the oil 574 is transferred to a feed chamber 584 of a film wipe apparatus 592. At the bottom of the feed chamber 584, a pump 586 pumps the oil via a feed line 588 and a check valve 590 into the short-path film wipe apparatus 592. Pump rates are typically 1000-1500 ml/hr, and depend on the $CO_2$ being given off, if any, the percentage of THCa converted to THC, and the vacuum pressure of the short-path film wipe apparatus 592. In the short-path film wipe apparatus 592, the oil is wiped in a thin film around the heated, inside wall 594 of the film wipe apparatus 592 by a blade 596. The inside wall 594 is heated via a temperature-maintained jacket. A cooler, condensing coil 598 condenses the target fraction, which leaves the film wipe apparatus 592 as a distillate via target discharge tube 600 and is collected in container 602. The residual liquids fall down the inside wall 594 of the film wipe 592 and exit through residual arm 604 to be collected in container 606. The film wiping occurs under reduced pressure provided by a vacuum pump connected to port 608 via a cold trap.

Using the system of the present invention it is possible to convert approximately 40 to 44 kg (88 to 97 lb) of raw cannabis plant material into pure or nearly pure distillate oil over a period of 16 hours. The apparatus and process may also be used for the extraction, refinement and distillation of waste plant material from processes that do not succeed in extracting all the valuable extracts. The apparatus and process may be scaled up depending on the amount of raw cannabis plant material to be treated.

G. Variations

While the best presently contemplated mode of carrying out the subject matter disclosed and claimed herein has been described, other modes are also possible.

In some embodiments, a spinning band fractional distillation apparatus is used instead of the short-pass film wipe apparatus for one or more of the film-wipe steps.

In some embodiments the ethanol is not chilled in step 112, which is omitted, and the ethanol added to the raw cannabis plant material at a temperature of 15-30° C. in step 115. In these embodiments, steps 127, 132 and 137 are omitted, as the ethanol is not chilled before paper filter stages 128, 133 and 138. Filtration is particularly important if the ethanol is used at room temperature. It has been found that 10% more extracts are obtained using room-temperature ethanol compared to using chilled ethanol, but that the filtration stage is significantly more onerous. This is also subjective to the type of plant material used, but it is known that non-chilled ethanol has a greater miscibility, which makes the ethanol less discriminative thus picking up more unwanted materials.

Optionally, once the cannabinoids have been extracted in step 180 or 468, they may be further run through the film wipe apparatus 592 in order to separate them into THC and CBD. In other embodiments, spinning band fractional distillation is used instead of the film wipe to separate the THC and CBD.

In other embodiments within the purview of the present invention, other plant materials besides cannabis may be processed. For example, hemp may be processed to result in a 95% pure CBD oil. The present invention has wide application in respect of other plants that produce phytochemicals of interest, such as for the extraction of cannabimimetics from lavender. Phytochemicals of interest include cannabinoids, terpenes, and flavonoids.

In some embodiments, the apparatus is portable so that it can be taken to the different sites of various plant growers, to be used on an as-needed basis.

In some embodiments, one or more further media treatment steps making use of an attapulgite clay, a bentonite clay and/or silica filtration media are added to the described media treatment setups.

The mechanical centrifuge 570 used to separate the oil and solvent mixture from the brine can be replaced by a gravity fed separatory funnel.

As an alternative to the film wipe step 468, a vacuum spinning band distillation or fractional distillation procedure can be used in order to remove four fractions, for example, as opposed to the single fraction from the film wipe process.

Ethanol of 99% purity or more can be used for the extraction process.

In some embodiments, to eliminate the brine wash step, anhydrous ethanol (≤0.005% water) is used instead of the more usual ethanol formula that is approximately 95% pure with 5% water. This reduces the need for more robust filtration post extraction. However, steps should be taken to avoid instantaneous water contamination when the anhydrous ethanol is exposed to air.

In some embodiments, the media treatment is omitted if a lower quality of cannabis oil is desired.

Temperatures that have been given to the nearest degree include all temperatures within a range of ±0.5° C. of the given value. Temperatures that have been given to the nearest 0.1° C. include all temperatures within a range of ±0.05° C. of the given value.

Other pore sizes of filter cartridges are used in other embodiments.

In other embodiments, the vacuum pressure of the rotovap in non-polar solvent reclamation step 464 is different from the range given above.

In some embodiments it is not necessary to completely remove the ethanol from the oil in ethanol reclamation step 454. It has been found that residual ethanol in the oil will absorb into the aqueous brine phase during the brine washing step 460. There is therefore no need for absolute removal of ethanol from the crude oil.

In some embodiments, non-polar solvents other than hexane, heptane and pentane are used.

In general, unless otherwise indicated, singular elements may be in the plural and vice versa with no loss of generality.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. For example, various pumps, valves, jackets and lines are not shown for clarity. Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. Steps in the flowchart may be performed in a different order, other steps may be added, or one or more steps may be removed without altering the main outcome of the process. All parameters, dimensions, materials, and configurations described herein are examples only and may be changed depending on the specific embodiment. Accordingly, the scope of the invention is to be construed in accordance with the substance defined by the following claims.

The invention claimed is:

1. A process for extracting cannabinoids from raw *cannabis* plant material comprising the steps of:
adding ethanol to dried and ground *cannabis* plant material to form an initial mixture;
centrifuging the initial mixture to separate a crude oil and ethanol mixture from the initial mixture;
treating the crude oil and ethanol mixture with charcoal particles, bentonite clay particles and magnesium oxide particles to remove unwanted components therefrom;
evaporating ethanol from the treated crude oil and ethanol mixture to leave oil;
washing the oil with brine;
heating the brine-washed oil to convert THCa (tetrahydrocannabinolic acid) in the brine-washed oil into THC (tetrahydrocannabinol), resulting in decarboxylated oil; and
distilling the decarboxylated oil to obtain cannabinoids.

2. The process of claim 1, further comprising the steps of:
adding a non-polar solvent to the oil before washing the oil with brine; and
evaporating the non-polar solvent after washing the oil with brine.

3. The process of claim 2, wherein the non-polar solvent comprises hexane, heptane or pentane.

4. The process of claim 2, further comprising, after washing the oil with brine and before evaporating the non-polar solvent, drying the oil with magnesium sulfate.

5. The process of claim 2, wherein:
the brine is 60-100% saturated with kosher sodium chloride;
the step of washing with brine comprises agitating the non-polar solvent, oil and brine for 5-30 minutes; and
the brine is removed by a centrifuge or gravity-fed separatory funnel.

6. The process of claim 5, wherein the ratio of non-polar solvent to oil to brine is 1:1:2 by volume.

7. The process of claim 2, wherein the heating step comprises passing the brine-washed oil through a short-path film wipe apparatus.

8. The process of claim 7, wherein the film wipe apparatus has:
a feed temperature of 100-115° C.;
a residue discharge arm temperature of 100-115° C.;

an inner wall surrounded by a jacket with a circulating fluid at a temperature of 160-175° C.; and a condensing coil temperature of 0° C. to −20° C.

9. The process of claim 2, wherein the heating step comprises heating the brine-washed oil to 90-110° C. in a vacuum oven.

10. The process of claim 1, further comprising the steps of:

drying the raw *cannabis* plant material; and grinding the raw *cannabis* plant material to result in the dried and ground plant material.

11. The process of claim 10, wherein the raw *cannabis* plant material is:

dried to a moisture content of 5%; and ground to an average particle size of ≤9000 μm.

12. The process of claim 1, wherein the centrifuging step occurs in a wash and spin-dry separator and has a duration of 8-15 minutes.

13. The process of claim 1, wherein:

the ethanol is at a temperature between −60° C. and 18° C. when it is added to the dried and ground *cannabis* plant material; and the ethanol is added to the dried and ground *cannabis* plant material in a ratio of 6.6-10 liters of ethanol to 1 kg of ground plant material.

14. The process of claim 1, wherein treating the crude oil and ethanol mixture comprises the steps of:

adding the charcoal particles to the crude oil and ethanol mixture, agitating the charcoal particles and crude oil and ethanol mixture, and filtering off the charcoal particles; then adding the bentonite clay particles to the crude oil and ethanol mixture, agitating the bentonite clay particles and crude oil and ethanol mixture, and filtering off the bentonite clay particles; and then adding the magnesium oxide particles to the crude oil and ethanol mixture, agitating the magnesium oxide particles and crude oil and ethanol mixture, and filtering off the magnesium oxide particles.

15. The process of claim 14, wherein:

filtering off the charcoal particles comprises filtering the charcoal particles and crude oil and ethanol mixture with a lenticular depth filtration apparatus;

filtering off the bentonite clay particles comprises filtering the bentonite clay and crude oil and ethanol mixture with a lenticular depth filtration apparatus; and filtering off the magnesium oxide particles comprises filtering the magnesium oxide particles and crude oil and ethanol mixture with a lenticular depth filtration apparatus.

16. The process of claim 15, wherein:

the crude oil and ethanol mixture is at a temperature between −10° C. and +85° C. when charcoal particles are added;

the charcoal particles are filtered off at a temperature between −10° C. and 50° C.; and the bentonite clay particles and the magnesium oxide particles are filtered off at a temperature between 10° C. and 50° C.

17. The process of claim 1, wherein the unwanted components are one or more of pigments, chlorophyll, fats, waxes, lipids, heavy metals and particulates.

18. The process of claim 1, wherein the distilling step comprises:

subjecting the decarboxylated oil to a first film wipe to remove volatile terpenes and leave a first residue;

subjecting the first residue to a second film wipe to remove non-volatile terpenes and leave a second residue; and subjecting the second residue to a third film wipe to obtain cannabinoids.

19. The process of claim 18, wherein:

the first and second film wipes are performed at a pressure of 0.001-0.01 mbar; and the third film wipe is performed at a pressure of 0.0008-0.003 mbar.

20. The process of claim 18, further comprising subjecting the cannabinoids to a further film wipe process to separate the cannabinoids into cannabidiol and tetrahydrocannabinol.

21. The process of claim 18, wherein:

the first film wipe is performed with:

a feed temperature of 100-115° C.;

a residue discharge arm temperature of 100-115° C.;

an inner wall surrounded by a jacket with a circulating fluid at a temperature of 140-145° C.; and a condensing coil temperature of 0° C. to −20° C.;

the second film wipe is performed with:

a feed temperature of 100-115° C.;

a residue discharge arm temperature of 100-115° C.;

an inner wall surrounded by a jacket with a circulating fluid at a temperature of 145-159° C.; and a condensing coil temperature of 20-60° C.; and the third film wipe is performed with:

a feed temperature of 100-115° C.;

a residue discharge arm temperature of 100-115° C.;

an inner wall surrounded by a jacket with a circulating fluid at a temperature of 140-165° C.; and a condensing coil temperature of 68-73° C.

22. The process of claim 1, wherein the raw *cannabis* plant material is *cannabis* flower.

23. The process of claim 1, wherein the raw *cannabis* plant material is *cannabis* leaves and stems.

24. The process of claim 1, wherein the step of distilling is performed using a spinning band distillation apparatus.

25. The process of claim 1, wherein the adding and centrifuging steps are performed simultaneously.

26. The process of claim 1, further comprising leaving residual ethanol in the oil after the evaporating step, wherein the step of washing with brine removes the residual ethanol from the oil.

27. The process of claim 1, wherein terpenes are obtained in the step of distilling.

28. The process of claim 18, further comprising subjecting the cannabinoids to a spinning band fractional distillation process to separate the cannabinoids into cannabidiol and tetrahydrocannabinol.

* * * * *